US006479039B1

(12) United States Patent
Dyer et al.

(10) Patent No.: US 6,479,039 B1
(45) Date of Patent: Nov. 12, 2002

(54) ANTIMICROBIAL ARTIFICIAL NAIL COMPOSITION AND METHODS FOR PREPARING AND USING SAME

(75) Inventors: David Dyer, Cypress; Kenneth B. Gerenraich, Seal Beach, both of CA (US)

(73) Assignee: Woodward Laboratories, Inc., Los Alamitos, CA (US)

( * ) Notice: Subject to any disclaimer, the term of this patent is extended or adjusted under 35 U.S.C. 154(b) by 0 days.

(21) Appl. No.: 09/352,292

(22) Filed: Jul. 13, 1999

(51) Int. Cl.[7] .................. A61K 7/043; A61K 47/32; A61J 25/10; A61J 25/34
(52) U.S. Cl. ........................... 424/61; 424/407
(58) Field of Search .................. 424/405, 61, 407, 424/409, 443; 524/533

(56) References Cited

U.S. PATENT DOCUMENTS

| | | | |
|---|---|---|---|
| 2,577,773 A | 12/1951 | Lambert | 252/152 |
| 3,419,006 A | 12/1968 | King | 128/268 |
| 3,968,246 A | 7/1976 | Merianos et al. | 424/330 |
| 4,203,872 A | 5/1980 | Flanagan | 252/542 |
| 4,278,664 A | 7/1981 | van Cleave | 424/148 |
| 4,321,277 A | 3/1982 | Saurino | 424/329 |
| 4,336,151 A | 6/1982 | Like et al. | 252/106 |
| 4,657,758 A | 4/1987 | Goldenberg et al. | 434/49 |
| 4,721,724 A | 1/1988 | Stettendorf et al. | 514/396 |
| 4,797,420 A | 1/1989 | Bryant | 514/643 |
| 5,181,914 A | 1/1993 | Zook | 604/307 |
| 5,284,833 A | 2/1994 | McAnalley et al. | 514/23 |
| 5,346,692 A | 9/1994 | Wohlrabet et al. | 424/61 |
| 5,362,422 A | 11/1994 | Masters | 252/544 |
| 5,439,682 A | 8/1995 | Wivell et al. | 424/401 |
| 5,661,170 A | 8/1997 | Chodosh | 514/390 |

FOREIGN PATENT DOCUMENTS

| | | |
|---|---|---|
| GB | 2108840 | 5/1983 |
| JP | 59-59601 | 4/1984 |
| WO | WO 87/03476 | 6/1987 |

OTHER PUBLICATIONS

Allantoin Product Information, Published by Sutton Laboratories,Inc.

Fisher, A.A., "Allantoin: A Non–Sensitizing Topical Medicament Therapeutic Effects of the Addition of 5 Percent Allantoin to Vaseline®", 1981, pp. 1–3.

Germaben® II–E Product Information, Published by Sutton Laboratories, Inc.

Katz, N.D., "Tough as Nails . . . Fugoid® Tincture", *Cutis*, May 1992.

Lubeck, D.P. et al, "Quality of life of persons with onychomycosis", *Quality of Life Res.*, 1993, 2, 341–348.

Sutton Laboratories, Inc., Fact Sheet on Allantoin, Jan. 1, 1992, pp. 1–6.

*Primary Examiner*—Edward J. Webman
(74) *Attorney, Agent, or Firm*—Woodcock Washburn LLP

(57) ABSTRACT

A composition for forming an antimicrobial artificial nail, a method for preparing the same, and a method for treating a microbial infection of a nail plate are provided. The composition comprises a binder component; a filler component which polymerizes to form an acrylic matrix subsequent to contact with the binder component; and an antimicrobial agent available for diffusion from the acrylic matrix.

24 Claims, No Drawings

ANTIMICROBIAL ARTIFICIAL NAIL COMPOSITION AND METHODS FOR PREPARING AND USING SAME

FIELD OF THE INVENTION

The present invention relates to a composition for forming an artificial fingernail, and to methods for preparing and using the same. In particular, the present invention relates to a composition for forming an artificial fingernail, and to methods for preparing and using the same, wherein the composition comprises an antimicrobial agent beneficial in treating and preventing the spread of infections of the nail area caused by bacteria, fungi and other microbes.

BACKGROUND OF THE INVENTION

Several compositions have been developed to produce an artificial fingernail which can be applied to a natural nail plate for the purpose of protecting, adorning, extending, and/or decorating the nail plate. In general, these compositions are formed from a liquid binder comprising the following ingredients:
  a) a monomeric acrylate of methacrylate ester such as methyl methacrylate, ethyl methacrylate, tetrahydrofufuryl methacrylate, methoxyethyl methacrylate, methoxyethoxyethyl methacrylate and similar others;
  b) a di, tri or multifunctional acrylate or methacrylate ester such as ethylenegylcol dimethacrylate, diethyleneglycol dimethacrylate, 1,4-butanediol dimethacrylate, trimethylolpropane trimethacrylate, and similar others; and
  c) a tertiary amine accelerator such as N,N-dimethyl-para toluidine.

The liquid binder is combined with a polymeric filler generally comprising the following ingredients:
  a) a finely divided polymeric methacrylate (e.g., poly(ethyl methacrylate)) or copolymeric methacrylate (e.g., a 70:30 molar ratio comprising poly(ethyl-co-methyl) methacrylate); and
  b) an organic peroxide polymerization initiator such as benzoyl peroxide.

The known compositions are used to form an artificial nail on a nail plate by dipping an application brush first in the liquid binder and then into the polymeric filler, so as to form a wetted mass on the brush. The wetted mass is then transferred to a prepared nail plate, where the wetted mass is manipulated to achieve the desired shape. Forms and molds may be positioned about the nail plate prior to application of the wetted mass to facilitate in extending the artificial nail beyond the nail plate.

The known compositions are based on the free-radical driven polymerization of acrylate monomers around acrylate polymers and/or copolymers. Accordingly, when the liquid binder is mixed with the solid polymer filler, the organic peroxide from the polymer filler interacts with the tertiary amine catalyst in the liquid binder to produce free radicals which catalyze the polymerization reaction. Polymerization speed may be regulated so as to yield acceptable times for working the wetted polymer filler into the desired shape by adjusting the concentrations of the initiator and accelerator present in the composition. Acceptable durations for total polymerization typically range from 3 to 5 minutes from the initiation of the reaction, a time short enough to decrease the likelihood of damage to the finished surface but long enough to allow the user sufficient time to shape the composition.

Optional components may be added to the general composition to impart specifically desired properties to the composition and/or the final product. For example, polymerization inhibitors (e.g., methyl ether of hydroquinone or butylated hydroxytoluene (BHT)), dyes, and ultraviolet light stabilizers are often added to the liquid binder. Likewise, pigments (e.g., titanium dioxide), secondary polymers (e.g., polyvinyl acetate), and flow property modifiers (e.g., fumed silica) are typically added to the polymeric filler.

Although the onset and speed of polymerization may be increased by increasing the levels of both the organic peroxide and the tertiary amine, an excess of these compounds may generate chromogenic substances during the polymerization reaction. Therefore the limiting consideration for improvement of the speed of polymerization is the concomitant discoloration which occurs when high levels of the organic peroxide and tertiary amine are used. To overcome the problem of discoloration, a non-yellowing composition for artificial nails has been described. The composition relies on the ability of free-hydroxyl moieties in the liquid binder to speed polymerization and initiation, thereby allowing lower concentrations of the organic peroxide and tertiary amine accelerator to be used. Hydroxyl groups are present in the formulation as saturated and/or unsaturated alcohols. A typical example of such a non-yellowing composition comprises a liquid binder and a polymer filler having the following compositions, in weight percent:

Liquid Binder Portion
  10–95% of a methacrylate monomer;
  1–50% of a methacrylate polymer crosslinker (e.g., multifunctional);
  1–50% of an alcohol (e.g., saturated or unsaturated methacrylate alcohols);
  0.1%–5% of a tertiary amine polymerization catalyst (e.g., dimethyl-p-toluidine and dihydroxyethl-p-toluidine); and
  Q.S. of a methyl-ethyl-hydroxyquinone (a polymerization inhibitor used as a regulator for product stability to prevent polymerization of the liquid binder prior to intended use)

Polymer Filler Portion
  95–99% of a finely divided polymer selected from the polyalkyl methacrylates and/or co-methacrylates;
  0.1–5.0% of an organic peroxide, such as benzoyl peroxide; and
  Q.S. of other ingredients such as whiteness enhancers (e.g., titanium dioxide and other pigments), secondary polymers (e.g., polyvinyl acetate) and flow modulators (e.g., fumed silica).

In addition, photopolymerizable compositions have been formulated. Those compositions contain an ultraviolet light-activated hardening accelerator to accelerate the polymerization reaction. Light-activated accelerators generally contain 40–90% of a monomer selected from the methyl, ethyl, propyl, isopropyl, n-butyl, isobutyl, tert-butyl, furfuryl, tetrahydrofurfuryl, and glycidal esters of acrylic acids, and the alkyl substituted acrylic acids in which the alkyl chain length is 1–4 carbons; 3–40% of a monomer selected from the group consisting of the esters of polyhydric alcohols having from about two to about four hydroxyl groups, and preferably acrylic acid or an alkyl-substituted acrylic acid in which the alkyl group has from one to four carbon atoms; and from 0.1–30%, and preferably from 0.2–5% by weight, of a photopolymerization initiator, such as benzoin, benzoin methyl ether, or other benzoin derivative.

Further, compositions have been described which reduce harmful or offensive odors associated with traditional artificial nail formulations. This class of acrylic nail preparation relies on alkylmethacrylate monomers (AMES) in addition to hydroxyalkyl methacrylates (HAMES) to temper odor production, as well as precipitous polymerization.

Regardless of the composition used, a problem associated with the known artificial nail compositions arises because the acrylic nails limit oxygen diffusion into, and $CO_2$ and water diffusion away from, the normally-permeable natural nail plate. In particular, a build up of water at the natural nail/artificial nail interface presents a warm, moist environment in which pathogens may thrive. Furthermore, organic solvents used in the artificial nail compositions can degrade the natural components of the nail which would normally prevent such infections. Therefore, moisture and biotic contaminants (e.g., bacteria, molds, spores, viruses and fungi) can become trapped on the nail plate, between the artificial nail and the nail plate, in the nail groove, and even in interstitial spaces between keratinocytes of the natural nail. The trapped contaminants can cause polymicrobial infections of the nail plate which result in discoloration and destabilization of the natural nail. Discoloration is of primary concern in the application of acrylic nails, whose thin polymer matrices are often translucent and reveal color defects of the natural nail. Destabilization of the natural nail plate increases the likelihood that mechanical sheer force on the attached artificial nail will cause painful tearing of the natural nail away from the living tissue of the nail bed. Onychomycosis is just one example of the myriad of microbial etiologies of nail disfigurement requiring expensive, prolonged medical therapy, which is not always innocuous and can even be toxic. Moreover, such therapy often provides less than satisfactory cure rates and patient tolerance. Additionally, from a commercial standpoint, professional nail technicians and consumers of professional nail care products recognize that lifting and chipping of artificial nails is exacerbated by organic contaminants which grow at the interface of the natural nail and the artificial nail.

In light of the foregoing, it would be highly beneficial to provide a composition for forming an artificial fingernail, and methods for preparing and using the same, wherein the composition and methods provide for prophylaxis against microbial infections of the nail plate due to the entrapment of organic contaminants on or beneath the artificial nail. Further, the composition and methods should provide a continued prophylaxis against acquired organic contamination after the application of the artificial nail. The composition and methods should also provide for an antimicrobial agent that is incorporated into the artificial nail but which is not covalently bound to the artificial nail so that the antimicrobial agent is available for diffusion from the artificial nail. Preferably, the composition and methods should enable the artificial nail to be formed prior to application of the artificial nail. The present invention is directed to these, as well as other, important needs.

SUMMARY OF THE INVENTION

This invention relates to compositions that are useful for forming antimicrobial, artificial fingernails, its method of manufacture and use. The antimicrobial compositions of the present invention are intended for use on vertebrate nail plates, and present a useful means of immediate decontamination and extended prophylaxis against polymicrobial infections of the nail plate.

One-aspect of the present invention provides a composition for forming an antimicrobial artificial nail comprising a binder component, a filler component which polymerizes to form an acrylic matrix subsequent to contact with the binder component, and an antimicrobial agent. Suitable antimicrobial agents for use in compositions of the present invention include, but are not limited to, antimicrobial quaternary amines and homologues thereof. Other similarly active antimicrobial agents known in the art can also be used in the composition of the present invention.

Another aspect of the present invention is a method for forming an antimicrobial artificial nail wherein a binder component is mixed with a filler component and an antimicrobial agent to form a pre-nail mixture. The pre-nail mixture is then fashioned into a predetermined shape and allowed to polymerize to form a matrix, wherein the antimicrobial agent is available for diffusion from the matrix.

Yet another aspect of the present invention is a method for treating a microbial infection of a nail plate wherein an antimicrobial, artificial nail is applied to the infected nail plate. The artificial nail is formed from a composition comprising a binder component, a filler component which polymerizes to form a matrix subsequent to contact with the binder component, and an antimicrobial agent.

Still another aspect of the present invention is an antimicrobial artificial nail formed by mixing a binder component, a filler component and an antimicrobial agent to form a pre-nail mixture. The pre-nail mixture is then fashioned into a predetermined shape and allowed to polymerize to form a matrix, wherein the antimicrobial agent is available for diffusion from the matrix.

Additional features and embodiments of the present invention will become apparent to those skilled in the art in view of the ensuing disclosure and appended claims.

DETAILED DESCRIPTION OF THE INVENTION

It has been discovered that antimicrobial agents can be advantageously incorporated within an artificial nail to provide prophylaxis against susceptible organic contaminants. The present invention provides an antimicrobial composition for artificial nails, and methods for manufacturing and using the composition. The antimicrobial composition of the present invention is intended for use on vertebrate nail plates, and presents a useful means of immediate decontamination and extended prophylaxis against polymicrobial infections of the nail plate.

The composition of the present invention comprises a liquid binder and a polymer filler, which polymerize to form a matrix when combined. The composition of the present invention is intended as an acrylic, artificial nail, and generally contains components known in the art for use in acrylic artificial nails. The composition further comprises one or more antimicrobial agents incorporated into the liquid binder, the polymer filler, or both. When the polymer filler and liquid binder ate combined and allowed to polymerize, the antimicrobial agent or agents become reversibly incorporated into the polymer matrix. Accordingly, the antimicrobial agent or agents are available for diffusion from the matrix to the surface of the artificial nail, and from the matrix down to the artificial nail/natural nail interface. The antimicrobial agent or agents would then be available for inhibitory and/or cidal action against microorganisms trapped beneath the artificial nail and/or present within the keratinous nail matrix.

Quantities presented herein as "percent by weight" or "weight percent" refer to the percent of a particular component in a composition based on the total weight of the composition. Quantities expressed as "percent" or "%" refer to "weight percent", unless specifically indicated otherwise.

The antimicrobial agents that can be incorporated into the present invention include agents commonly used for such applications which are chemically compatible with this invention in general. They may be incorporated either into the liquid binder or polymer filler of the invention, based upon the physicochemical properties of the antimicrobial selected. The antimicrobial agents used in this invention are employed at concentrations known to be effective as hard surface antimicrobial agents, e.g., agents commonly used in counter-top disinfectant formulations. Such antimicrobial agents are generally of low volatility, such that they are not lost to evaporation, and are retained in both the fluid and solid states of the invention. Their antimicrobial activity is detectable after the transition of the invention from the fluid to the solid state (i.e., after polymerization).

In preferred embodiments of the present invention, the antimicrobial agent comprises a benzalkonium chloride (BAC) compound. The BAC compound can be in the form of a mixture of homologues, such as that defined by the United States Pharmacopacia, an individual homologue, or misture of preferred homologues. Benzalkonium chloride compounds suitable for use in the composition of the present invention include the most antimicrobially active species of benzalkonium chloride, corresponding to the general formula:

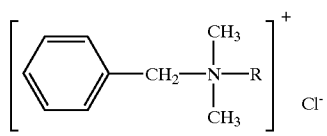

wherein R is an alkyl group having from 10 to 17 carbon atoms, and preferably from 12–14 carbon atoms.

Exemplary suitable BAC homologues that may be used in the present invention include N,N-dimethyl-decyl ammonium chloride, N,N-dimethyl-undecyl ammonium chloride, N,N-dimethyl-dodecyl ammonium chloride, N,N-dimethyl-tridecyl ammonium chloride, N,N-dimethyl-tetradecyl ammonium chloride, N,N dimethyl-pentadecyl ammonium chloride, N,N-dimethyl-hexadecyl ammonium chloride, and N,N-dimethyl-heptadecyl ammonium chloride.

When a BAC compound is used as the antimicrobial agent, the composition of the present invention preferably contains at least about 85 percent by weight, preferably about 90 percent by weight, more preferably about 95 percent by weight and most preferably about 98 percent by weight of the preferred BAC homologues, wherein R is an alkyl group having from 10 to 17 carbon atoms, or a mixture thereof. The total content of the BAC compound in the antimicrobial composition of the present invention ranges from between about 0.05 to 5 percent by weight.

Other antimicrobial agents that may be used in the composition of the present invention, either alone or in combination, include the general class of antimicrobial quaternary amines and related compounds, such as, for example, monoalkyl-trimethyl ammonium salts, dialkyl ammonium salts, heteroaromatic ammonium salts, polysubstituted quaternary ammonium salts, bis-quaternary ammonium salts and polymeric quaternary ammonium salts. The total content of these compounds in the composition of the present invention is preferably between about 0.05 to 5.0 percent by weight.

Yet other antimicrobial agents, also referred to as germicidal agents, that may be used, either alone or in combination, in the composition of the present invention include the general class of phenols, which includes cresols and resorcinols. Phenols in concentrations of approximately 0.2, 1.0, and 1.3 percent by weight are bacteriostatic, bactericidal, and fungicidal, respectively. While it is not intended that the present invention be bound by any particular theory, it is believed that the germicidal action of phenols is achieved at these concentrations through protein denaturation. The phenol-protein interaction is relatively weak, allowing the phenol molecule to penetrate deep into the tissue. This quality of phenol allows phenol to penetrate dense, intact keratinous matrices, such as the stratum corneum or the nail plate. When employed, the total content of phenol in the composition of the present invention is between about 0.05–5.0 percent by weight, preferably between about 0.1–2.5 percent by weight, and more preferably between about 0.3–1.0 percent by weight.

Several phenol derivatives are more potent than phenol itself, and the most important among these are the halogenated phenols and bis-phenols, the alkyl-substituted phenols, and the resorcinols. Examples of these latter species useful in the composition of the present invention include resorcinol, hexylresorcinol, hexachlorophene, parabens, thymol, chlorothymol, parachlorometaxylenol, orthophenylphenol, p-tertiary butylphenol, p-tertiary amylphenol, o-benzylphenyl-p-chlorophenol, parachlorophenol, camphorated parachlorophenol, tetrabromomethylphenol, and 2,6-dimethyl-4-chlorophenol.

Yet other antimicrobial agents suitable as germicides in the composition of the present invention are antimicrobial biguanides. This class of germicide is compatible with the BAC compounds and are believed to function by causing cellular death through the disruption of the infecting microorganism's cell membrane. Exemplary suitable biguanides include chlorhexidine gluconate and its acetate derivative. These compounds may be employed in the present invention, either alone or in combination, in amounts from between about 0.05–5.0 percent by weight, preferably between about 0.1–4.5 percent by weight, and more preferably between about 1.0–4.0 percent by weight.

Also suitable for use as germicides in the composition of the present invention are antimicrobial furan derivatives. The presence of a nitro- group at the five position of the 2-substituted furans confers antimicrobial activity to this class of compounds. An example of this class of molecule that is suitable for use in the composition of the present invention is nitrofurazone. Antimicrobial furan derivatives may be incorporated into the present invention at concentrations of between about 0.05–5.0 percent by weight, preferably between about 0.1–3.0 percent by weight, and more preferably between about 0.5–2.0 percent by weight.

Yet other antimicrobial agents that may be used in the composition of the present invention, either alone or in combination, include antimicrobial dyes. Examples of suitable antimicrobial dyes include the triphenyl-methane hexamethylrosaniline chloride, and tetramethylthionine chloride. Antimicrobial dyes may be incorporated into the composition of the present invention in concentrations ranging from between about 0.01–2.0 percent by weight, preferably between about 0.02–1.5 percent by weight, and more preferably between about 0.025–1.0 percent by weight.

Other antimicrobial agents known in the art are also suitable for use in the composition of the present invention. Table 1 lists exemplary pharmacologic compounds which may be used, either alone or in combination, in the context of the present invention as an antimicrobial agent. In addition to specific examples of antimicrobial agents discussed above those skilled in the art will recognize that other antimicrobial agents, which are compatible with other components of the composition of the present invention, can also be used in the composition of the present invention. Such antimicrobial agents are effective against polymicrobial infections by various mechanisms of action. Suitable antimicrobial agents are effective, for example, against infections caused by dermatophytic fungi, yeast, bacteria, and molds. The active agents listed in Table 1 may be incorporated into the composition of the present invention, either singly or in combination with any other described antimicrobial agents, in amounts ranging from between about 0.05–5.0 percent by weight, preferably between about 0.1–3.0 percent by weight, and more preferably between about 0.5–2.0 percent by weight.

TABLE 1

Antimicrobial agents useful in the composition of the present invention

| Generic | Product | Manufacturer |
|---|---|---|
| A. Agents useful in treating dermatophyte infections | | |
| Amorolfine | Loceryl | Roche |
| Econazole-nitrate | Spectazole | Ortho |
| Naftifine | Naftin | Herbert Labs |
| Oxiconazole | Oxistat | Glaxo |
| Sulconazole | Exelderm | Westwood-Squibb |
| Terbinafine | Lamisil | Novartis |
| Tolnaftate | Tinactin | Schering-Plough |
| Undecylinic acid | Desinex | Pharmacraft |
| Undecylinic acid | Gordochrom | Gordon Labs |
| Griseofulvin | Fulvicin | Schering |
| Itraconazole | Sporonox | Janssen |
| Fluconazole | Diflucan | Pfeizer |
| B. Agents useful in treating yeast infections | | |
| Nystatin | Mycostatin | Westwood-Squibb |
| C. Agents useful in treating dermatophyte yeast and bacterial infections | | |
| Ciclopirox olamine | Loprox | Hoechst-Roussel |
| Clotrimazole | Lotrimin | Schering-Plough |
| Econazole-nitrate | Spectazole | Ortho |
| Haloprogin | Halotex | Westwood-Squibb |
| Micronazole | Micatin/monistat Derm | Ortho |
| Micronazole | Fungoid Tincture | Pedinol |
| Benzalkonium chloride | Mycocide NS | Woodward Laboratories |
| D. Agents useful in treating non-dermatophyte (Saprophyte) opportunistic infections | | |
| Amphotercin B | Fungizone | Bristol-Myers Squibb |
| Ketoconazole | Nizoral | Janssen |
| Benzalkonium chloride | Mycocide NS | Woodward Labs |
| Fluconazole | Diflucan | Roerig-Pfizer |
| Itraconazole | Itraconazole | Janssen |
| E. Agents useful in treating deep (systemic) mycotic infections | | |
| Flucytosine | Ancobon | Roche |
| F. Agents useful in treating actinomycetes infections | | |
| Amikacin | Amikin | Apothecon |
| Ampicillin | Omnipen | Wyeth-Ayerst |
| Ampicillin | Polycillin | Apothecon |
| Ampicillin | Principen | Apothecon |
| Penicillin-G | Bicillin | Wyeth-Ayerst |
| Penicillin-G | Wycillin | Wyeth-Ayerst |
| Terracycline | Doxycycline | Laderle |
| Trimethoprim | Bactrim | Roche |
| Sulfamethoxazole | Septra | Glaxo-Wellcome |

In one embodiment of the composition in accordance with the present invention, the liquid binder includes an alkyl- or aryl-methacrylate monomer in an amount ranging from about 10–95%, including but not limited to methyl-, ethyl-, n-butyl-, isobutyl-, n-propyl-, isopropyl-, tert-butyl-, methoxyethoxyethyl-, ethoxyethoxyethyl-, benzyl-, and phenethyl-methacrylate and combinations thereof; optionally and preferably about 1–50% of a di, tri, or multifunctional methacrylate crosslinker, including but not limited to ethylene glycol, dimethacrylate, diethylene-glycol dimethylacrylate, triethylene glycol dimethacrylate, tetraethylene glycol dimethacrylate, poly(ethylene glycol) dimethacrylate, 1,3-dibutanediol dimethacrylate, 1,4-butanediol dimethacrylate, 1,6-hexanediol dimethacrylate, 1,12-dodecanediol dimethacrylate, neopentyl glycol dimethacrylate, trimethylolpropane trimethacrylate and combinations thereof; from about 1–50% of an unsaturated or saturated alcohol compound, including but not limited to hydroxyethl methacrylate, hydroxypropyl methacrylate, hydroxybutyl methacrylate, propylene glycol monomethylether, diethylene glycol monoethylether, isopropyl alcohol, propylene glycol, monomethacrylate and combinations thereof; and from about 0.1–5% of a tertiary amine polymerization accelerator selected from the group including but not limited to N,N-dimethyl-p-toluidine, N,N-dihydroxethyl-p-toluidine, N,N-dimethyl aniline, and 4-(dimethylamino)phenethyl alcohol. Optionally, a polymerization inhibitor, such as butylated hydroxytoluene or methyl ether of hydroxyquinone, can be employed at concentrations shown to be effective in the art to prevent the premature reaction of monomers prior to use.

The polymer filler comprises: about 95–99.9% of a finely-divided polymer selected from the group including but not limited to poly(ethyl methacrylate), poly(methyl methacrylate), poly(ethyl co-methyl methacrylate), poly(butyl co-methyl methacrylate), poly(vinyl-acetate), poly(vinyl-butyral), poly(ethyl-co-butyl methacrylate); and about 0.1–5% of an organic peroxide catalysis initiator, preferably benzoyl peroxide. Optionally, the polymer filler may also contain low amounts of secondary polymers, such as finely-divided poly-(vinyl acetate). When used the secondary polymers are preferably present in amounts of between about 0.1–1%.

Pigments and other coloring agents are optionally used for enhancement of the esthetic qualities of embodiments of the present invention. Colors and pigments useful in artificial nail compositions are well known to those skilled in the art. Compiled lists of such components are available from the United States Food and Drug Administration. Examples of suitable coloring agents for use in compositions of the present invention include the insoluble lakes and colored polymeric material, opacity regulating agents such as titanium dioxide and aluminum silicate, tinting agents such as iron oxide, and pearlescent agents such as guanine bismuth oxychloride. Specific examples of pigments compatible with compositions of the present invention include D&C Red 6, D&C Red 30, D&C Red 36, D&C Red 9, D&C Red 7, FD&C Yellow 5, and FD&C Yellow 6.

The amount of pigment used in the composition can vary, but generally does not exceed about 15 percent by weight, based on the total weight of the composition. For improved wear resistance, the pigment concentration should not be lower than about 3 percent by weight. In compositions of the present invention, the amount of pigments and/or other coloring agents, if the coloring agents are not pearlescent, is preferably from about 0.05 percent to about 6 percent by weight, more preferably from about 0.1 percent to about 5.5 percent by weight, and still more preferably from about 0.5 percent to about 5 percent by weight. Suitable amounts of pearlescent components range from about 0.5 percent to about 15 percent by weight, preferably from about 1 percent to about 12.5 percent by weight and more preferably from about 2 percent to about 11 percent by weight.

Ultraviolet (UV) light-absorbing agents can be used in the compositions of the present invention to inhibit photolysis of susceptible chemical compounds and thereby minimize concomitant discoloration of the finished formulation. Any suitable UV blocker, or combination of blockers, commonly used in non-aqueous nail coating formulations can be used in the composition of the present invention. Specific examples include Uvinul (BASF), benzophenone and derivatives thereof, and FD&C and D&C colors known to absorb UV radiation. The amount of UV absorbing agent in compositions of the present invention can range from about 0.01 percent to about 2 percent by weight, preferably from about 0.05 percent to about 1 percent by weight, and more preferably from about 0.06 to about 0.5 percent by weight.

Suspension and/or viscosity regulating agents can be used to facilitate the ease of application of the compositions of the present invention, and to improve uniformity of flow. Appropriate suspension agents include dimethyl dioctadecyl ammonium bentonite, benzyl dimethyl hydrogenated tallow ammonium montmorillonite, and dimethyl dioctadecyl ammonium hectorite. Appropriate viscosity regulating agents that may be used include fumed silica and pulverized glass. The amount of suspension/viscosity regulating agents used can be from about 0.05 percent to about 10 percent by weight, preferably from about 0.2 percent by weight to about 7 percent by weight, and more preferably from about 1 percent to about 4 percent by weight. If desired, in addition to or instead of the above-mentioned compounds, the viscosity may be further regulated through the addition of polyvalent acids, such as orthophosphoric acid, in an amount from about 0.05 percent to about 7 percent by weight, preferably from about 0.25 percent to about 6 percent by weight and more preferably from about 0.5 percent to about 2 percent by weight.

Lipids can be included in the composition of the present invention. Lipids are important to the functioning of the nail plate as a barrier. However, lipids can be stripped from the nail by organic solvents normally used in nail care preparations. It is known that lipids can be applied to dried, hardened nail coatings and can enhance the shine of the coatings. However, it has been discovered that lipids can be incorporated directly into artificial nail composition. The presence of lipids in artificial nail compositions can help to ameliorate the depletion of lipids from the nail. Furthermore, while it is not intended that the present invention be bound by any particular theory, it is believed that lipids incorporated into artificial nail compositions can diffuse from the interior of the nail coating to the air/coating surface and/or the nail/coating surface over time, thus continuing to enhance shine and provide benefits to the nail.

Generally, any lipids compatible with the composition of the present invention can be used. Suitable lipids are well known to those skilled in the art. Exemplary suitable lipids for use in the compositions of the present invention include phospholipids, such as phosphatidylcholine, phosphatidylinositol, phosphatidyl serine and phosphatidylethanolamine, lysophospholipids such as lysophosphatidic acid, fatty acids, cholesterol, cholesterol esters, waxes, squalene, triglycerides and sphingolipids. In particular, suitable sphingolipids include ceramide sphingosine, sphingomyelin, and glycolipids including cerebrosides. If present, the concentration of lipids in the composition of the present invention is preferably from about 0.001 weight percent to about 2 weight percent, more preferably from about 0.001 to about 1 weight percent, and even more preferably from about 0.01 to about 0.5 weight percent.

If desired, oils can be included in the composition of the present invention. For example, tea tree oil is compatible with the composition of the invention and can be used therein. Also suitable are one or more individual components of tea tree oil, such as terpinen-4-ol, alpha terpineol, alpha pinene, and combinations thereof with or without tea tree oil. Such components can be derived from natural sources, or can be synthesized using methods known to those skilled in the art. Oils can be present in an amount from about 0.01 weight percent to about 20 weight percent, preferably from about 0.05 weight percent to about 5 weight percent, and even more preferably from about 0.1 weight percent to about 3 weight percent.

If desired, the composition of the present invention can include vitamins, proteins and growth promoters, either alone or in combination. The vitamins are nutrients needed by the cells of the nail matrix that are involved in the production of keratin and the formation of new nail plate tissue. Exemplary suitable vitamins include lipid soluble vitamins, such as the tocopherols, phytonadione, menaquinone, menadione, retinol, 3-dehydroretinol; and various amphiphylic water soluble vitamins, such as cholecalciferol. Other optional components include amphiphylic amino acids and peptides compatible with the compositions of the present invention. Also suitable are agents that are known to promote the growth of fibroblasts and keratinocytes and are compatible with the compositions of the present invention, such as the phosphatidates, and lyso-derivatives such as lysophosphatidic acid. Vitamins, proteins and growth promoters, as a group, can be present in the compositions of the present invention in amounts from about 0.001 percent to about 5 percent by weight, preferably from about 0.01 percent to about 3 percent by weight, and more preferably from about 0.05 percent to about 2 percent by weight.

Other optional components include emollients and mitigators of inflammation. Emollients and mitigators are added to limit the deleterious effects of the organic solvents used in the composition of the present invention. For example, compositions using methyl methacrylate tend to produce artificial nails which are so strongly bonded to the natural nail that the natural nail can easily be damaged when removing the artificial nail. Also, methyl methacrylate produces harmful vapors which can trigger inflammatory responses upon prolonged exposure. Emollients and mitigators are beneficial in reducing these unwanted effects of methyl methacrylate. Exemplary suitable emollients and mitigators include allantoin, its metallic salts, and organic conjomers. Emollients and mitigators can be employed in amounts ranging between about 0.001–5.0 percent by weight, preferably between about 0.01–3.0 percent by weight, and more preferably between about 0.05–2.0 percent by weight.

One or more solvents can be used to facilitate suspension of solid components in the composition of the present invention. The solvents are preferably non-aqueous. Such solvents are well known to those skilled in the art, and exemplary types of solvents compatible with the composition of the present invention include alkanes, alkanols, ketones, esters including acetates, amides, ethers, alcohols, glycol-ethers and nitroparaffins. Specific examples of these types of solvents include ethyl ether, petroleum ether, methyl acetate, acetone, cyclohexane, ethyl acetate, methyl ethyl ketone, carbon tetrachloride, ethyl alcohol, n-butyl acetate, isobutyl acetate, amyl acetate, xylol, isopropyl alcohol, butyl alcohol, diethylene glycol monomethylether, diethylene glycol monoethylene ether and ethyl lactate. Also suitable as solvents are acyclic aliphatic and cycloaliphatic compounds. Aldehydes and ketones are not preferred for use as solvents in the compositions of the present invention. The amount of solvent present in the composition can be from about 10 percent to about 80 percent by weight, preferably from about 15 percent to about 60 percent by weight, and more preferably from about 38 percent to about 50 percent by weight. When alcohols are used as solvents, it is preferred that the solvent include one or more alcohols in combination with one or more non-alcoholic solvents. For example, a suitable solvent can advantageously comprise one or more alcohols, especially isopropyl alcohol, and one or more esters, such as butyl acetate and/or ethyl acetate. Generally, it is preferred that the amount of alcohol be less than about 20 percent by weight and more preferably less than about 15 percent by weight, based on the total weight of the composition.

In an alternate embodiment of the present invention, the composition of the present invention comprises a hardening accelerator. The hardening accelerator is used to accelerate the polymerization process. Hardening accelerators suitable for use in the composition of the present invention include ultraviolet light-activated compositions. A light-activated composition in accordance with the present invention contains 40–90% of a monomer selected from the methyl, ethyl, propyl, isopropyl, n-butyl, isobutyl, tert-butyl, furfuryl, tetrahydrofurfuryl, and glycidal esters of acrylic acids, and the alkyl substituted acrylic acids in which the alkyl chain length is 1–4 carbons; 3–40% of a monomer selected from the group consisting of the esters of polyhydric alcohols having from about two to about four hydroxyl groups, and preferably acrylic acid or an alkyl-substituted acrylic acid in which the alkyl group has from one to four carbon atoms; and from 0.1–30%, and preferably from 0.2–5% by weight, of a photopolymerization initiator, such as benzoin, benzoin methyl ether, or other benzoin derivative. Preferred photopolymerization initiators comprise the dioxolane compounds of the formula:

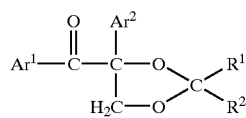

in which $R^1$ and $R^2$ are H or any organic radical having a molecular weight of 210 or less; and $Ar^1$ and $Ar^2$ are selected from phenyl, napthyl and non-sterically hindered substituted phenyl or napthyl radicals in which the substituents each have a molecular weight of 210 or less. The species

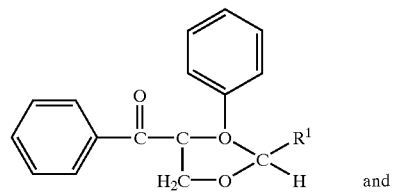 and

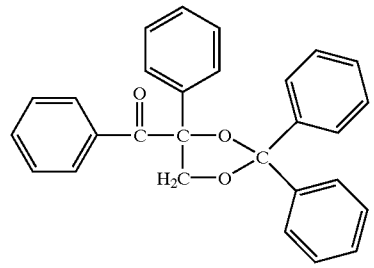

are particularly preferred. The photopolymerization initiator may be mixed with from 5–25%, and preferably 12–18%, of a modifier which is soluble or swellable when mixed with the photopolymerization initiator and which acts to improve elasticity. The modifier is preferably selected from the class of particulate cured elastomers, including methacrylate modified butadiene styrene block copolymer (Blendex BTA III's, Borg-Watner Co. Parksberg W.Va.), or from a mixture of elastomer and particulate cellulose esters or cellulose ether-esters at a ratio of at least 4.5:1.

In another alternate embodiment of the present invention, the composition comprises a so-called "odorless" acrylic nail system, which produces little or no vapor during polymerization, and which is not prone to catastrophic crystallization. This class of acrylic nail preparation relies on alkylmethacrylate monomers (AMES) in addition to hydroxyalkyl methacrylates (HAMES) to temper odor production, as well as precipitous polymerization. The alkyl moieties of the HAMES are 1–4 carbons in length and are used in a ratio of 3–10:1, in the finished composition. The preferred alkyl side chain length is ethyl in both the HAME and AME. Other useable compounds include those HAMEs and AMEs with methyl, propyl, and butyl (n-, iso- and tert-) moieties. These compounds are contained in the liquid binder portion of the composition. A small amount of unbranched or branched materials (usually less than 1%) may be present without significantly affecting the composition. The polymer filler in this case would contain conventional catalysts, including benzoyl peroxide, and polymeric alkylmethacrylates, including polymeric ethyl methacrylate, polymeric hydroxyethyl methacrylate, copolymeric ethyl methacrylate/hydroxyethyl methacrylate, polymeric methyl methacrylate, or copolymeric ethyl methacrylate/methyl methacrylate. Accelerators and/or inhibitors of the polymerization reaction are also acceptable ingredients for this type of composition.

The present invention further relates to a method for forming an antimicrobial artificial nail. The method comprises the step of selecting a polymer binder, a liquid filler, and antimicrobial agent, wherein the polymer binder, the liquid filler, and the antimicrobial agent are selected to form a composition in accordance with the present invention. The polymer filler, liquid binder, and antimicrobial agent are then combined to form a pre-nail mixture. In a preferred embodiment, the pre-nail mixture is formed by combining between about 50% and about 80% of the ploymer filler, between about 20% and about 50% of the liquid binder, and between about 0.01% and about 5% of the antimicrobial agent. In an even more preferred embodiment, the pre-nail mixture is formed from between about 55% and about 65% of the polymer filler and between about 35% and about 45% of the liquid binder. The pre-nail mixture is then applied to a prepared nail plate and manipulated to form a predetermined shape. Forms or molds can be positioned about the nail plate-to aid in shaping the pre-nail mixture. The pre-nail mixture is then allowed to polymerize to form a matrix, wherein the antimicrobial agent is incorporated within the matrix and available for diffusion from the matrix. Alternatively, the pre-nail mixture can be applied to a carrier or a mold where it is allowed to polymerize to form the matrix. The matrix can then be mechanically removed from the mold or carrier and secured to the nail plate using conventional techniques known in the art, such as by adhesives. It would be appreciated by those skilled in the art that the liquid binder and polymer filler can be assembled and packaged separately for sale, to be combined on site by the user. Alternatively, the liquid binder and polymer can be mixed and shaped to form the artificial nail prior to packaging for sale.

The artificial nail can be used to treat a microbial infection of a nail plate by applying the artificial nail to the infected nail plate. The artificial nail is applied to the nail plate either directly, as when the mixture polymerizes directly on the nail, or with adhesives, as when the artificial nail is formed and then secured to the nail plate.

EXAMPLES

The following examples are merely illustrative of the present invention and should not be considered limiting of the scope of the invention in any way. These examples, and equivalents thereof, will become more apparent to those skilled in the art in light of the present disclosure and the accompanying claims.

1. Preparation of Artificial Nail Compositions

Artificial nail compositions were prepared to demonstrate the effectiveness of an incorporated antimicrobial agent. The liquid binder and polymer filler components used were prepared as follows:

| Liquid Binder: | |
|---|---|
| Ethyl methacrylate | 83% |
| Propylene glycol | 7% |
| Ethylene glycol dimethacrylate | 6% |
| N,N-dimethyl-p-toluidine | 1% |
| Antimicrobial agent | 3% |
| TOTAL: | 100% |
| Polymer Filler: | |
| Poly (ethyl-co-methyl) methacrylate (70:30 mole ratio) | 98.6% |
| Benzoyl peroxide | 1.4% |
| TOTAL: | 100.0% |

The liquid binder and polymer filler were used to prepare three separate formulations. Formulation A was prepared as a control and, therefore did not contain an antimicrobial agent. Formulation B was prepared using 3% of a BAC compound (specifically, N,N-dimethyl-benzyl tetradecylammonium chloride) as the antimicrobial agent. Formulation C was prepared using 3% of a halogenated phenolic antimicrobial compound (specifically, chloroxylenol) as the antimicrobial agent.

Formulations A, B, and C were tested as follows. For each formulation, 600 mg of polymer filler and 400 mg of liquid binder (with or without antimicrobial agent)were mixed and allowed to dry as a film upon a sterile, non-frosted borosilicate glass slide for 24 hours. Each of the formulations yielded a polymer which was adherent to natural nails, resistant to chipping and, therefore, satisfactory in performance as an artificial nail. The resulting polymer film was shaped such that its maximum thickness was between 1–2.5 mm and that its overall surface area was approximately 6.25 $cm^2$. The film was removed mechanically from the slide and placed into 1 ml of sterile, distilled phosphate buffered saline contained in a sterile, polycarbonate 15 ml conical centrifuge tube. A 500 microliter aliquot of the aqueous extract was innoculated with 50 microliters of a 1:10 dilution of Serratia marcescens stock culture (density equivalent to a 0.5 McFarland nephelometric standard in Mueller-Hinton cation-adjusted growth medium) and incubated for 30, 60, 300 and 600 seconds. Incubations were terminated by pipetting 20 microliters of the incubation solution into 200 microliters of Letheen broth. Neutralization confirmation was performed according to the Official Methods of Analysis of the Association of Official Analytical Chemists protocol 991.47. Forty microliters of the neutralized solution was plated, via a spread plate technique, onto tryptic soy agar plates and read after 8 hours of incubation at 37° C. Bacterial growth was assessed by counting colony forming units (cfu). Colony forming units were enumerated as single, distinct colonies of bacterial growth as per standard procedure (National Committee for Clinical Laboratory Standards. Methods for dilution antimicrobial susceptibility tests for bacteria that grow aerobically. $3^{rd}$ Edition Approved Standard NCCLS document M7A3). The data for Formulations A, B, and C are given in Table 2 below.

TABLE 2

| | Bacterial Count (cfu) | | |
|---|---|---|---|
| Time: | Formulation A | Formulation B | Formulation C |
| 30 seconds | >1000 cfu | 0 cfu | 0 cfu |
| 60 seconds | >1000 cfu | 0 cfu | 0 cfu |
| 300 seconds | >1000 cfu | 0 cfu | 0 cfu |
| 600 seconds | ~540 cfu | 0 cfu | 0 cfu |

The data in Table 2 clearly illustrate that the formulations containing N,N-dimethyl-benzyl tetradecylammonium chloride and chloroxylenol, Formulations B and C, caused a significantly greater reduction of bacteria than did the non-antimicrobial formulation, Formulation A. Specifically, Formulations B and C produced an acrylic polymer that contains antimicrobial activity after 24 hours of drying sufficient to cause $\geq 3$ $\log_{10}$ reduction in Serratia marcescens populations. Accordingly, amphiphilic and hydrophobic antimicrobial therapeutic reagents are suitable for effective use in accordance with the present invention.

It should be noted that chloroxylenol is a phenol derivative and N,N-dimethyl-benzyl tetradecylammonium chloride (BAC) is a quaternary amine, and phenol derivatives are expected to be more compatible with the generally non-aqueous, non polar environment of the current invention. However, it is important to note that BAC, which would be expected to be more compatible with an aqueous, polar environment, is also stable in the formulation prepared according to the present invention. This illustrates the wide range of chemical properties tolerated by the composition of the present invention, and the compatibility of the composition with a large number of antimicrobial active agents.

Those skilled in the art will appreciate that numerous changes and modifications may be made to the preferred embodiments of the invention and that such changes and modifications may be made without departing from the spirit of the invention. For example, although the examples are directed toward ethyl methacrylate formulations, the present invention is equally suited for use with methyl methacrylate, non-yellowing, and "odorless" formulations. It is therefore intended that the appended claims cover all equivalent variations as fall within the true scope and spirit of the invention.

What is claimed is:

1. A composition for forming an antimicrobial artificial nail comprising, in weight percent:

between about 20% and about 50% of a binder component comprising a methacrylate monomer;

between about 50% and about 80% of a filler component comprising a polymer and a catalysis initiator, wherein said filler component and said binder component form an acrylic matrix when reacted; and between about 0.01% and about 5% of an antimicrobial agent available for diffusion from said acrylic matrix.

2. The composition of claim 1 wherein the antimicrobial agent is incorporated in to the binder component.

3. The composition of claim 1 wherein the antimicrobial agent is incorporated into the filler component.

4. The composition of claim 1 wherein the antimicrobial agent comprises a quaternary amine.

5. The composition of claim 4 wherein the antimicrobial agent is selected from the group consisting of monoalkyl-trimethyl ammonium salts, dialkyl ammonium salts, heteroaromatic ammonium salts, polysubstituted quaternary ammonium salts, bis-quaternary ammonium salts, and polymeric quaternary ammonium salts.

6. The composition of claim 5 wherein the antimicrobial agent comprises benzalkonium chloride, a homologue of benzalkonium chloride, or a mixture thereof.

7. The composition of claim 6 wherein the antimicrobial agent comprises N,N-dimethyl-decylammonium chloride, N,N-dimethyl-undecylammonium chloride, N,N-dimethyl-dodecylammonium chloride, N,N-dimethyl-tridecylammonium chloride, N,N-dimethyl-tetradecylammonium chloride, N,N-dimethyl-pentadecylammonium chloride, N,N-dimethyl-hexadecylammonium chloride, N,N-dimethyl-heptadecylammonium chloride, or a mixture thereof.

8. The composition of claim 1 wherein the antimicrobial agent comprises phenols, halogenated phenols, bis-phenols, alkyl-substituted phenols, cresols, resorcinols, or a mixture thereof.

9. The composition of claim 1 wherein the antimicrobial agent comprises a biguanide.

10. The composition of claim 1 wherein the antimicrobial agent comprises a furan derivative.

11. The composition of claim 1 wherein the antimicrobial agent comprises an antimicrobial dye.

12. The composition of claim 1 wherein the antimicrobial agent comprises a tertiary amine catalyst.

13. The composition of claim 1 wherein the antimicrobial agent comprises an organic peroxide.

14. A method for forming an antimicrobial artificial nail comprising the steps of:

a. mixing a binder component comprising a methacrylate binder, a filler component comprising a finely-divided polymer and a catalysis initiator, and an antimicrobial agent to form a pre-nail mixture;

b. forming the pre-nail mixture into a predetermined shape; and c. allowing the pre-nail mixture to polymerize to form a matrix wherein the antimicrobial agent is available for diffusion from the matrix.

15. A method for treating a microbial infection of a nail plate comprising the step of applying to the nail plate an artificial nail formed from a composition:

a. a binder component comprising a methacrylate binder;

b. a filler component comprising a finely-divided polymer and a catalysis initiator, wherein the filler component polymerizes to form a matrix subsequent to contact with the binder component; and c. an antimicrobial agent available for diffusion from the matrix.

16. An artificial nail formed by a process comprising the steps of:

a. mixing a binder component comprising a methacrylate binder, a filler component comprising a finely-divided polymer and a catalysis initiator, and an antimicrobial agent to form a pre-nail mixture;

b. forming the pre-nail mixture into a predetermined shape; and c. allowing the pre-nail mixture to polymerize to form a matrix wherein the antimicrobial agent is available for diffusion from the matrix.

17. The composition of claim 1 wherein the antimicrobial agent is incorporated into the binder component.

18. The composition of claim 1 wherein the antimicrobial agent is incorporated into the filler component.

19. The composition of claim 1 wherein the antimicrobial agent comprises a quaternary amine.

20. The composition of claim 19 wherein the antimicrobial agent is selected from the group consisting of monoalkyl-trimethyl ammonium salts, dialkyl ammonium salts, heteroaromatic ammonium salts, polysubstituted quaternary ammonium salts, bis-quaternary ammonium salts, and polymeric quaternary ammonium salts.

21. The composition of claim 20 wherein the antimicrobial agent comprises benzalkonium chloride, a homologue of benzalkonium chloride, or a mixture thereof.

22. The composition of claim 1 wherein the antimicrobial agent comprises an antimicrobial dye.

23. The composition of claim 1 wherein the antimicrobial agent comprises a tertiary amine catalyst.

24. The composition of claim 1 wherein the antimicrobial agent comprises an organic peroxide.

* * * * *